United States Patent [19]

Glenn

[11] 4,005,711
[45] Feb. 1, 1977

[54] INHALATION DEVICE
[75] Inventor: Albert Glenn, San Francisco, Calif.
[73] Assignee: Syntex Puerto Rico, Inc., Humacao, P.R.
[22] Filed: Jan. 13, 1975
[21] Appl. No.: 540,918
[52] U.S. Cl. .............................. 128/266; 128/208; 128/206
[51] Int. Cl.² ...................................... A61M 13/00
[58] Field of Search .......... 128/266, 265, 198, 199, 128/200, 201, 206, 207, 208, 185; 222/193

[56] References Cited
UNITED STATES PATENTS

| | | | |
|---|---|---|---|
| 1,406,903 | 2/1922 | Rose | 128/266 |
| 2,029,408 | 2/1936 | Bramsen et al. | 222/193 |
| 2,507,702 | 5/1950 | Fields | 128/266 |
| 2,549,303 | 4/1951 | Friden | 128/206 |
| 2,587,215 | 2/1952 | Priestly | 128/206 |
| 3,858,583 | 1/1975 | Hallworth et al. | 128/266 |
| 3,888,253 | 6/1975 | Watt et al. | 128/266 |

Primary Examiner—Robert W. Michell
Assistant Examiner—Henry J. Recla
Attorney, Agent, or Firm—Joseph I. Hirsch; William B. Walker

[57] ABSTRACT

An inhalation device having an elongate housing having a passageway for the passage of air therethrough. The passageway, of relatively small diameter, opens into an emptying chamber, of relatively greater diameter, adjacent that end of the housing which is adapted for insertion into the mouth or nose of the user. Adjacent that end of the emptying chamber closest to the passageway, the housing has means for receiving or presenting a unit dose of powdered medicament for administration. During inhalation, a portion of the air stream passing through the passageway into the emptying chamber is deflected by a beveled deflector causing sufficient air flow to come into contact with the powdered medicament whereby the powdered medicament is entrained in the air stream being inhaled, and is carried into the nose, throat or lungs of the user where beneficial or therapeutic action of the medicament occurs.

18 Claims, 3 Drawing Figures

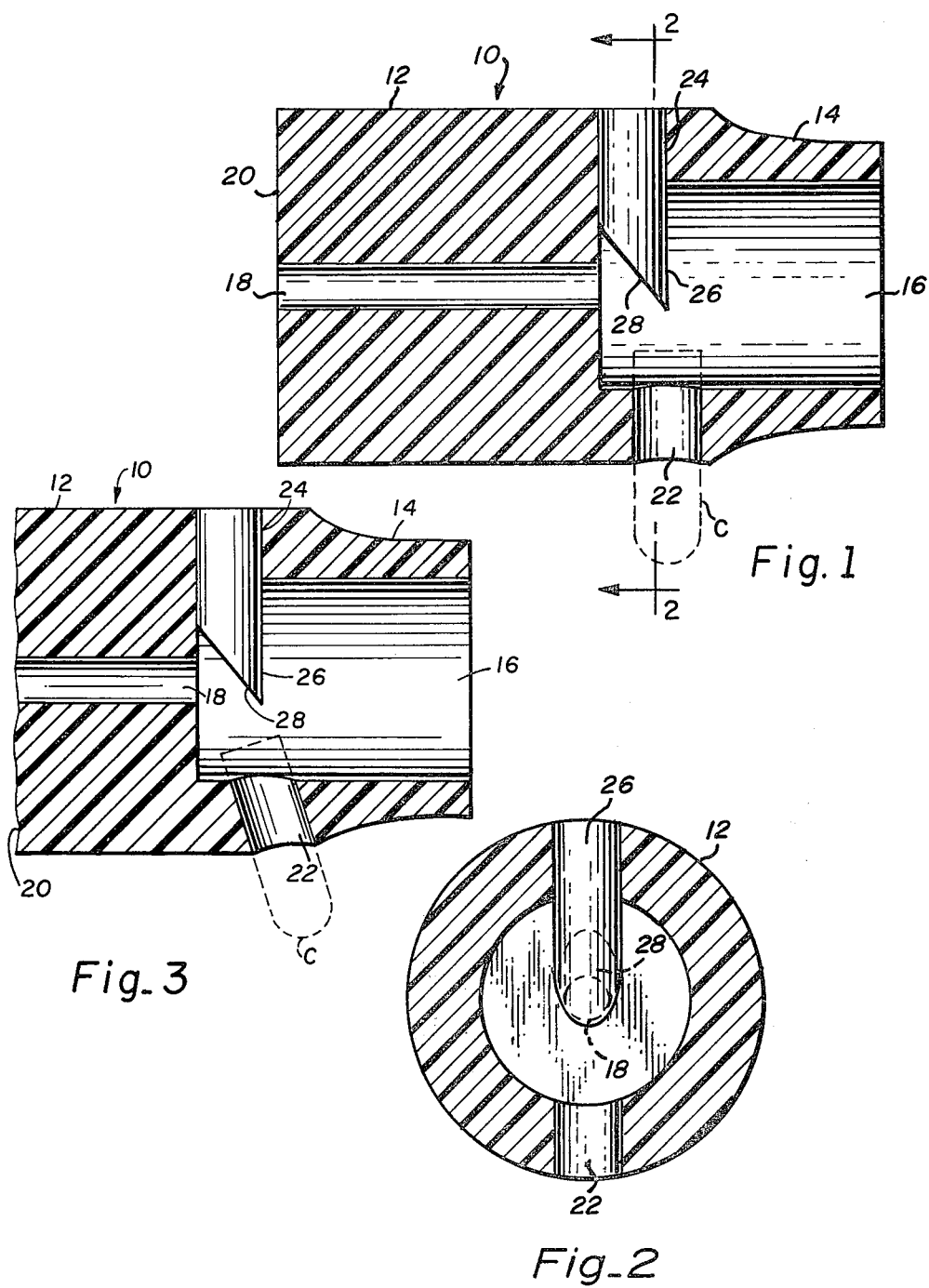

INHALATION DEVICE

FIELD OF THE INVENTION

This invention is related to devices for the administration of powdered medicaments by inhalation. More particularly, this invention relates to an inhalation device having, in the essential aspects thereof, no moving parts, yet which is capable of causing a powdered medicament, held within a container inserted into or adjacent to, the device, to be rapidly and effectively dispensed from the container, entrained in the air stream being inhaled and, thusly, carried into the nose, throat or lungs of the user where beneficial action of the medicament occurs.

BACKGROUND OF THE INVENTION

Known, prior art inhalation devices include, for example, those shown in U.S. Pat. Nos. 988,352; 2,507,702; and 2,603,216; and Great Britain Pat. No. 1,118,431.

SUMMARY OF THE INVENTION

The inhalation devices of the present invention include an elongate housing having a longitudinal passageway for the passage of air therethrough, one end of the housing being adapted for insertion into the mouth or nose of a user. The passageway, of relatively small diameter, opens into an emptying chamber, of relatively greater diameter, adjacent the output end of the housing. Adjacent that end of the emptying chamber closest to the passageway, the housing includes means for receiving or presenting a unit dose of powdered medicament for administration. As shown, the housing has a port adapted to receive and hold a powdered medicament-holding container. A beveled deflector is disposed adjacent the means for holding the container and, during inhalation, a portion of the air stream passing along the passageway into the emptying chamber is deflected by the beveled deflector into the container holding the medicament, whereby the powdered medicament in the container is entrained in the air stream being inhaled, and is carried into the nose, throat or lungs of the user where beneficial or therapeutic action of the medicament occurs. The medicament will be deposited in either the nose, throat or lungs depending upon the nature and size of the medicament particles and the embodiment of the device used to administer the medicament (e.g., a device with a mouthpiece will be utilized for administration of medicaments to the lungs, etc.).

In one embodiment, the axes of the deflector and the container port are off-set, with the axis of the deflector being closer to the passageway, to divert a portion of the air flow along the passageway into the medicament-holding capsule. The off-set distance (along the longitudinal axis of the device) is, in part, determined by the diameter of the passageway, the air flow rate through the device (as determined by the lung capacity and lung strength of the user), the angle of the beveled surface makes with the long axis of the deflector and the distance between the lower edge of the deflector and the upper edge of the container. However, by appropriate selection of the design parameters, the axes need not be off-set, it being adequate if the deflector diverts a portion of the air flow sufficient to empty the medicamentholding container. In addition, the container port can be tilted (up to 30° from the vertical) toward the passageway (i.e., away from the output end of the housing) to further assist in causing the powdered medicament to be expelled from the container. All such design parameters can be varied singly or in combination to achieve desired medicament administration.

Container, as used herein, is intended to include any means by which a unit dose of medicament is presented to the device for administration. Capsules are the presently preferred form of containers; however, it is contemplated that other forms would be equally suitable if appropriate structural modifications of the device, to accommodate the different carrier, are made as, and if, necessary.

The container, in one aspect of the present invention, is manually opened, just prior to insertion into the device, to expose the medicament as is necessary for entrainment during inhalation. Optionally, in another aspect of this portion of the invention, the device can have means associated therewith for opening the container after it has been inserted into the device or for automatically opening the container as it is being inserted into the device. In either case, such means eliminate the need to manually open the container prior to insertion and, thusly, reduce the possibility of inadvertent spillage of the medicament prior to inhalation.

It has been found that, with the inhalation devices of this invention, the powdered medicament held within the container is rapidly and efficiently entrained in the air stream passing though the device during inhalation, and, as such, is carried into the nose, throat or lungs of the user for beneficial action of the medicament to occur.

BRIEF DESCRIPTION OF THE DRAWINGS

The foregoing and still further features and advantages of the present invention will become more apparent from the following detailed description, taken together with the accompanying drawings wherein:

FIG. 1 is a vertical cross-sectional view of the inhalation device of the present invention;

FIG. 2 is a cross-sectional view of the inhalation device of FIG. 1 taken along line 2—2 of FIG. 1; and FIG. 3 is a vertical cross-sectional view of an alternate embodiment of the inhalation device of the present invention.

In the discussion below, reference will be made to a capsule as the exemplary container for presenting the medicament to the device for administration. As set forth above, other containers are contemplated for use with the device described herein.

Referring to FIG. 1, there is shown an inhalation device 10 having a substantially cylindrical housing 12 (as can best be seen in FIG. 2). At one end of housing 12 is a mouthpiece 14 intended for insertion into the mouth of a user thereof. Mouthpiece 14 can be redesigned to permit insertion into the nasal passages or, if desired, an adapter (not shown) can be placed over the mouthpiece to permit nasal use. Adjacent mouthpiece 14 is an emptying chamber 16 connected at the inner end thereof to passageway 18 which extends through to the other end 20 of the device. The manner of connecting passageway 18 with chamber 16 can be squared-off as shown, or more streamlined, if desired, as long as the particular configuration selected is effective to cause the powdered medicament to be expelled from the capsule during the desired number of inhalations. If desired, passageway 18 can initiate in an incoming or entrance chamber (not shown) of similar dimension and configuration to emptying chamber 16. Adjacent the lower, inner end of chamber 16, there is an opening or port 22 into which a half-opened capsule C, as shown in dotted outline in FIG. 1, is inserted prior to inhalation. Opposite port 22 there is a cylindrical passageway 24 in which there is inserted a beveled deflector 26. Optionally, the deflector can be fabricated directly as part of a unitary-type device. Deflector 26 has a beveled or slanted surface 28 which deflects a portion of the air stream passing through the device during inhalation into capsule C. The deflector can be inserted from different positions as long as a sufficient portion of the air stream is deflected into the capsule to cause the powdered medicament to be dispensed therefrom. Upon inhalation, the air passing through the device, including the portion deflected into the capsule, promptly and effectively causes the powdered medicament to be expelled from the capsule, entrained in the air stream passing through the device and, as such, carried into the throat or lungs of the user for beneficial or therapeutic action thereof to occur.

Referring to FIG. 3, there is shown an alternate embodiment of the inhalation device of the present invention wherein port 22 is tilted (up to 30° from the vertical) toward the passageway (i.e., away from the output end of the housing) to further assist in causing the powdered medicament to be expelled from the container. Numerals in FIG. 3 which are common to FIGS. 1 and 2 are intended to designate like elements of the inhalation device.

In use, the patient manually opens the medicament-holding capsule or other medicament-holding container, and inserts the half-opened medicament-holding portion thereof into port 22, essentially to the position shown in dotted line in FIG. 1. The mouthpiece is then taken into the mouth and, upon inhalation, the air flowing through the device causes the medicament to be expelled from the capsule and entrained in the air stream flowing through the emptying chamber 16. In this manner, the medicament is carried into the throat or lungs of the user for beneficial or therapeutic action to occur.

As set forth above, means can be provided to open the medicament-holding carrier after it has been inserted into the device or to automatically open the container upon insertion thereof into port 22. For example, a slide having a sharp cutting edge can be manually pushed against the top of the medicament-holding carrier, while held within the device, to slice open the top thereof and thereby expose the medicament to be administered. Or the capsule, as it is being inserted, can be made to contact a sharp edge which will cut off the top of the capsule and, as with the prior means, expose the contents thereof. In either case, these means, and other means equivalent thereto, eliminate the need to manually open the container prior to insertion thereof into the inhalation device. This, in turn, reduces the possibility for spillage of the medicament prior to inhalation.

The entire device can be made of metal but preferably is made of suitable plastic material, such as nylon, polyacetal or polypropylene. With the exception of the capsule or other medicament-holding container, the device in its basic elements, is preferably of unitary construction, although multi-piece construction is contemplated, especially where the deflector is separately provided or where means are provided to open the medicament-holding container. The beveled deflector is also preferably made from plastic, such as from those referred to above. The device of this invention can be manufactured quite readily, thereby effecting substantial cost reduction in the manufacturing process, without adversely affecting medicament administration during inhalation.

The physical properties of each medicament formulation (i.e., the ability to fluidize and the flow characteristics thereof) will affect the ease or manner in which it is dispensed with these or other inhalation devices. However, for a given powdered formulation, varying the diameter of passageway 18, the positioning of port 22 (from the position as shown toward the open end of chamber 16), the angle of the beveled surface, the depth to which the deflector extends above or below the longitudinal axis of passageway 18, the height above the inside of emptying chamber 16 to which the medicament-holding container extends, and/or, in general, modification of the overall configuration and shape of chamber 16 and passageway 18, the devices can be made to deliver the medicament in a different number of inhalations or in a longer or shorter period of time, depending upon the nasal or lung capacities and strengths of each particular user. Quite obviously, no single device will be optimal for all persons requiring administration of powdered medicaments since, for example, people with differing lung capacities and strengths are known to generate flow rates from about 30 liters/minute or so to about 120 liters/minute or so through inhalation devices of this and known types. Nonetheless, the devices of this invention afford such variability through proper selection of the various design parameters listed above, that a device, embraced within the scope of this invention, can be designed for a particular patient-generated flow rate to deliver the medicament according to a certain set of pre-determined objectives (e.g., slow or fast administration, one or more inhalations, etc.). The net result is that a family of devices, all embraced within the present invention, can be designed, each of which will deliver the medicament under a different, given set of selected administration conditions. Conversely, the devices of this invention can be designed to cover an extensive range of operating contitions and thus be suitable for use by a variety of persons having differing inhalation abilities or capacities.

While the present invention has been described with reference to specific embodiments thereof, it will be understood by those skilled in this art that various changes may be made and equivalents may be substituted without departing from the true spirit and scope of the invention. Additionally, other modifications may be made to adapt a particular situation, material or composition of matter, structural desirability, or then-present objective to the spirit of this invention without departing from its essential teachings.

What is claimed is:

1. A breath-actuated inhalation device for dispensing a medicament from a medicament-holding container comprising a housing having a passageway for the movement of air therethrough, one end of said housing being an output end adapted for insertion into the mouth or nasal passages of a user thereof; said passageway terminating in an emptying chamber adjacent the output end of said housing, the cross-sectional area of said passageway being less than the cross-sectional area of said emptying chamber; aperture means extending through a side wall of said housing and opening into said emptying chamber for receiving a medicament-holding container; and means extending into said emptying chamber adjacent the interface thereof with said passageway and transversely thereto a distance into the projected air flow path of the air stream exiting from said passageway for deflecting only a portion of the air being drawn through said passageway during inhalation into said aperture means whereby, during inhalation, only a portion of the air drawn through said passageway is deflected by said deflecting means into a medicament-holding container held within said aperture means to cause medicament held therein to be dispensed therefrom.

2. The device of claim 1 wherein said means for receiving a medicament-holding container comprises a first opening in said housing adjacent said emptying chamber.

3. The device of claim 2 wherein said first opening is tilted toward said passageway.

4. The device of claim 2 wherein said first opening is tilted toward said passageway at an angle up to about 30° from the vertical.

5. The device of claim 2 wherein said deflecting means comprises a second opening in said housing adjacent said emptying chamber, and a deflection member supported by said second opening, said deflection member having a beveled surface at the end thereof closest to said first opening, said beveled surface facing the direction of air flow through said passageway during inhalation and serving to deflect a portion of the air being drawn through said passageway during inhalation toward said first opening.

6. The device of claim 5 wherein said second opening is opposite said first opening.

7. The device of claim 5 wherein said deflection member is movable within said second opening.

8. The device of claim 5 wherein the longitudinal axis of said second opening is off-set from the longitudinal axis of said first opening, the axis of said first opening being closer to the output end of said housing than is the axis of said second opening.

9. The device of claim 1 wherein said deflecting means comprises a deflection member having a beveled surface at the end thereof closest to said passageway, said beveled surface facing the direction of air flow through said passageway during inhalation and serving to deflect a portion of the air being drawn through said passageway during inhalation toward said aperture means.

10. The device of claim 9 wherein the plane of said beveled surface is at an angle of about 30° to about 60° with the longitudinal axis of said deflection member.

11. The device of claim 9 wherein the means for receiving a medicament-holding container comprises a first opening in said housing adjacent said emptying chamber, said first opening being tilted toward said passageway at an angle up to about 30° from the vertical.

12. A breath-actuated inhalation device for dispensing a medicament from a medicament-holding container comprising a housing having a passageway for the movement of air therethrough, one end of said housing being an output end adapted for insertion into the mouth or nasal passages of a user thereof; said passageway terminating in an enlarged emptying chamber adjacent the output end of said housing, the cross-sectional area of said passageway being less than the cross-sectional area of said emptying chamber; a first opening extending through a side wall of said housing and opening into said emptying chamber for receiving a medicament-holding container; deflector means extending into said emptying chamber adjacent the interface thereof with said passageway for deflecting only a portion of the air being drawn through said passageway during inhalation into said first opening, said deflector means comprising a deflection member having a beveled surface at the end thereof closest to said first opening, said beveled surface facing the direction of air flow through said passageway during inhalation, the plane of said beveled surface being at an angle of about 30° to about 60° with the longitudinal axis of said deflection member, said beveled surface serving to deflect a portion of the air being drawn through said passageway during inhalation toward said first opening whereby inhalation through said output end causes air flow along said passageway, only a portion of which is deflected by said deflector means into a medicament-holding container held within said first opening to cause medicament held therein to be dispensed therefrom.

13. The device of claim 12 where said first opening is tilted toward said passageway at an angle up to about 30° from the vertical.

14. The device of claim 12 wherein said deflection member is positioned within a second opening in said housing.

15. The device of claim 14 wherein said deflection member is movable within said second opening.

16. The device of claim 12 wherein the longitudinal axis of said second opening is off-set from the longitudinal axis of said first opening, the axis of said first opening being closer to the output end of said housing than is the axis of said second opening.

17. The device of claim 12 wherein said container receiving means is adapted to securely hold a medicament-holding container so as to prevent movement thereof during inhalation.

18. The device of claim 1 wherein said container receiving means is adapted to securely hold a medicament-holding container so as to prevent movement thereof during inhalation.

* * * * *